United States Patent [19]

Hartmann

[11] 4,412,729

[45] Nov. 1, 1983

[54] VISION TESTING DEVICE

[75] Inventor: Erwin Hartmann, Munich, Fed. Rep. of Germany

[73] Assignee: Optische Werke G. Rodenstock, Munich, Fed. Rep. of Germany

[21] Appl. No.: 207,801

[22] Filed: Nov. 17, 1980

[30] Foreign Application Priority Data

Nov. 16, 1979 [DE] Fed. Rep. of Germany ....... 2946325

[51] Int. Cl.³ .............................................. A61B 3/00
[52] U.S. Cl. ................................. 351/239; 351/237; 351/243
[58] Field of Search ....................... 351/13, 16, 17, 30, 351/31, 32, 36, 222, 237, 239, 243

[56] References Cited

U.S. PATENT DOCUMENTS

| 2,321,915 | 6/1943 | Higley | 351/28 |
| 2,738,701 | 3/1956 | Hudson | 351/237 |
| 3,684,355 | 8/1972 | Molner | 351/36 |
| 4,155,638 | 5/1979 | Wolbarsht | 351/246 |

Primary Examiner—R. A. Rosenberger
Attorney, Agent, or Firm—Craig & Burns

[57] ABSTRACT

A vision testing device, wherein projected or transilluminated indicia in the form of characters and/or symbols of different sizes and recognizabilities are shown to a subject under a test in a test field. The characters or symbols appear bright with a luminance of preferably about 70 cd/m². A darker field surrounds the characters or symbols, with the darker field having a luminance of about one-fifth to one-eighth of the luminance of the characters or symbols. Brighter areas with a luminance of 250–1000 cd/m² are provided adjacent the darker surrounding field.

12 Claims, 4 Drawing Figures

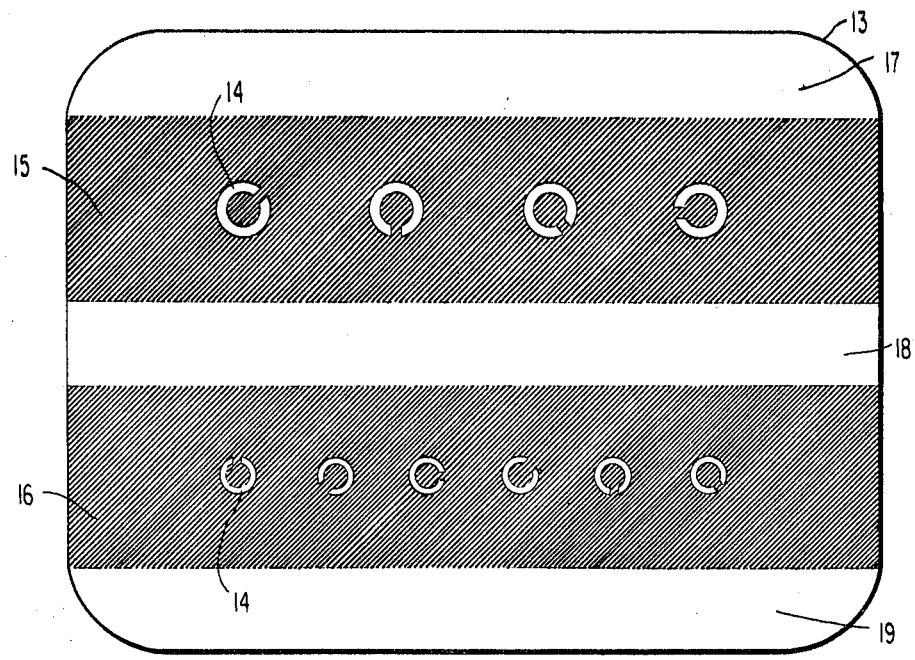
FIG.3
FIG.4
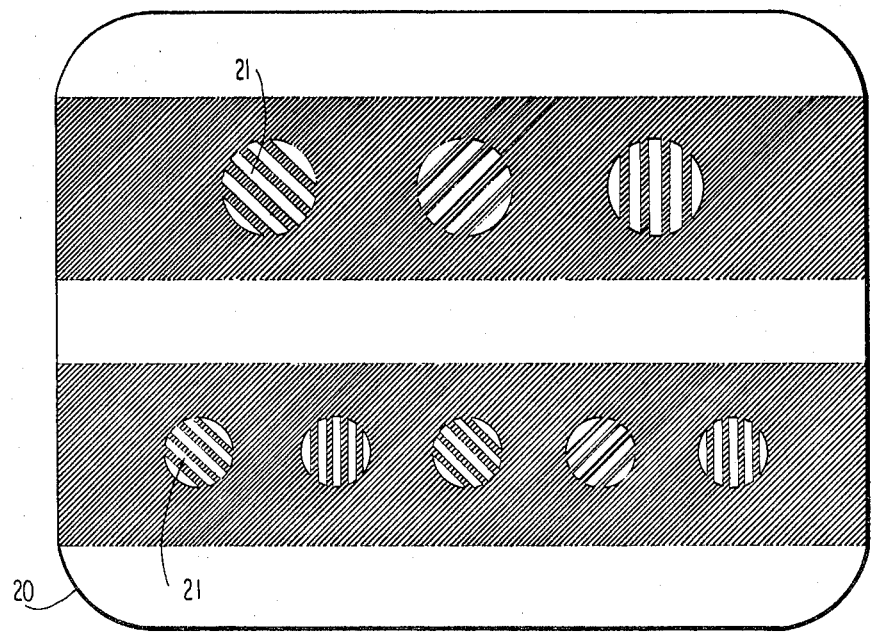

VISION TESTING DEVICE

The present invention relates to a testing device and, more particularly, to a vision testing device wherein projected or transilluminated characters and/or symbols of different sizes and recognizabilities are shown to a subject under test in a test field.

In order to test the vision of a subject, a method has been proposed wherein dark letters or other symbols are presented with a high contrast against a more or less bright surrounding area. This form of presentation to the subject simulates the stress to which the eye is subjected to during conventional reading.

In studies to determine visual acuity in road traffic situations, methods have been proposed for example, German Offenlegungsschrift No. 23 21 570) which involve showing the subject being tested, in addition to a test field, a source of dazzle light, controlled by a diaphragm, located outside the test field.

The above-noted studies which are easily performed and are widely used, provide hardly any information about the causes of possible deterioration of vision such as, for example, deterioration resulting from age-related cloudiness of the ocular media. Additionally, such studies also provide no information about the ability of an individual being tested to work with cathode ray tube (CRT) terminals, as viewed, for example, with data-processing equipment.

The aim underlying the present invention essentially resides in providing a vision testing device, preferably with the use of conventional vision testing apparatus, wherein the test conditions resemble those conditions to which the eye is subjected to when working with an electronic CRT terminal.

In accordance with advantageous features of the present invention, on the test field, the characters or symbols appear bright and preferably have a luminance of about 70 cd/m$^2$, in a darker surrounding field having a luminance of about one-fifth to one-eighth of the bright characters, and brighter areas, with the luminance of about 250–1000 cd/m$^2$, being provided adjacent to the surrounding field.

In a preferred embodiment of the present invention, the surrounding field has the luminance of approximately 10 cd/m$^2$ with the characters or symbols having a luminance of approximately 70 cd/m$^2$ and the brighter areas having a luminance of about 500 cd/m$^2$.

In accordance with further features of the present invention, the characters or symbols within the test field shown are arranged in one or more horizontal rows and are surrounded by surrounding field areas in the form of strips, with brighter areas above and below.

By virtue of the provision of a test field divided in accordance with the present invention, the test field may be shown in the usual fashion either individually or in pairs in test devices of the viewing type and may also be projected.

In accordance with the present invention, the test field which is shown may include a plurality of horizontal strips serving as surrounding fields for a corresponding number of letters or rows of symbols, for example, line patterns or Landolt rings, whereby the symbols offer different degrees of difficulty as far as their recognizability is concerned.

The strips which comprise the surrounding field are adjacent to brighter areas in the test field which results in a certain dazzle within the actual test plane. This dazzle has a disturbing effect upon individuals who have slightly clouded ocular media so that such a clouded ocular media becomes clear with the aid of the testing device in accordance with the present invention.

Moreover, the vision testing device of the present invention, together with results from other conventional vision tests, indicates whether the subject can reasonably be expected to work at electronic CRT terminals.

Accordingly, it is an object of the present invention to provide a vision testing device which provides information about the ability of an individual being tested by the device to work with cathode ray terminals.

Another object of the present invention resides in providing a vision testing device which enables the obtaining of information as to whether the individual being tested has a couldiness of the ocular media.

These and other objects, features, and advantages of the present invention will become more apparent from the following description when taken in connection with the accompanying drawings which show, for the purpose of illustration only, several vision testing devices in accordance with the present invention, and wherein:

FIG. 3 is a plan view of a further test field in accordance with the present invention provided with symbols as test character; and FIG. 4 is a plan view of yet another test field in accordance with the present invention provided with symbols as test characters.

Figure 1:
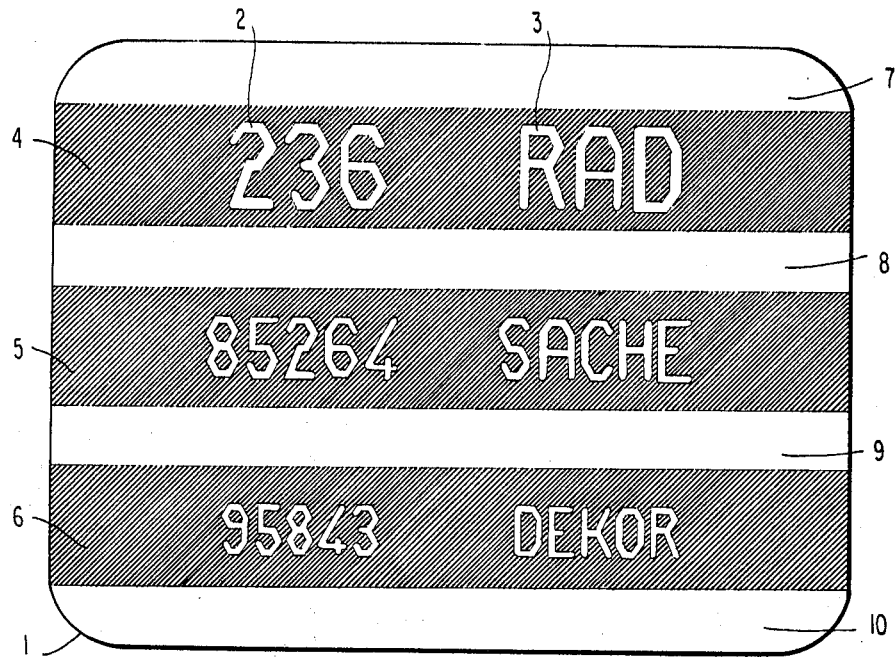
FIG. 1 is a plan view of a test field of a testing device in accordance with the present invention with indicia such as numbers and letters provided therein.

Referring now to the drawings and, more particularly, to FIG. 1, according to this Figure, a test field 1 is provided with numbers 2 and letters 3 as optotypes. The numbers 2 and letters 3 are of three different sizes. Each size of the optotype is arranged in a separate surrounding field strip 4, 5 and 6, with brighter areas 7, 8, 9, and 10 disposed adjacent to each surrounding field strip 4, 5, and 6.

The numbers 2 and letters 3 may have a luminance of approximately 70 cd/m$^2$, with surrounding area strips 4, 5, and 6 having a luminance of about 10 cd/m$^2$. The brighter areas 7, 8, 9, and 10 may have a luminance of about 500 cd/m$^2$.

Figure 2:
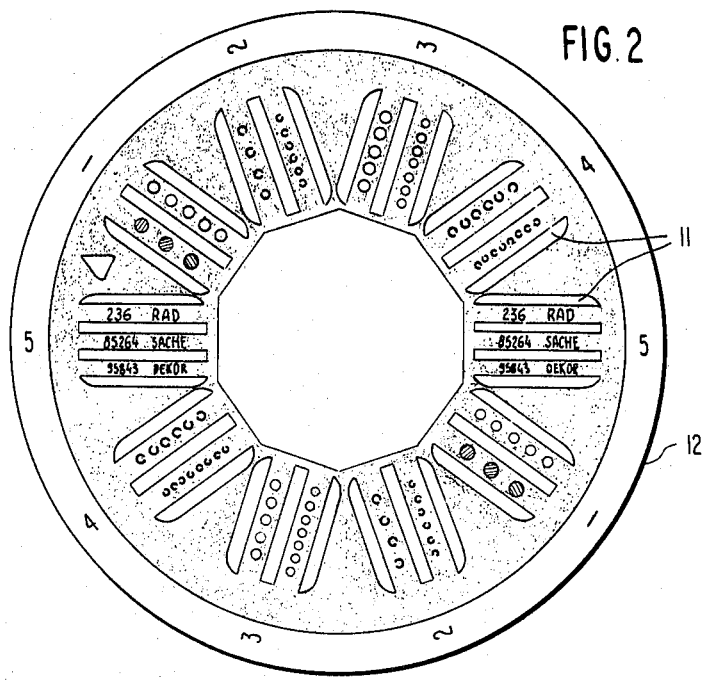
FIG. 2 is a plan view of a pairwise arrangement of test fields in accordance with a further embodiment of the present invention in a circular test disc for use in a vision-testing device of the viewing type.

FIG. 2 provides an example of a test field arrangement provided on a test disc 12 which is adapted to be used in a conventional viewing type vision testing device. As shown in FIG. 2, the test disc 12 is provided with five equal test fields 11 arranged in pairs located centrally in the circular test disc 12.

As shown in FIG. 3, a test field 13 is provided which includes two rows of Landolt rings 14 of different sizes within two surrounding field strips 15, 16 having brighter areas 17, 18, 19 arranged adjacent thereto. The luminances of the test fields of FIGS. 2 and 3 correspond to those of the arrangement in FIG. 1.

FIG. 4 provides an example of a test field 20 which corresponds in its arrangement to that shown in FIG. 3; however, line-like gratings 21 are employed instead of the Landolt rings 14.

While I have shown and described several embodiments in accordance with the present invention, it is understood that the same is not limited thereto but is susceptible of numerous changes and modifications as known to one having ordinary skill in the art and I therefore do not wish to be limited to the details shown and described herein, but intend to cover all such modifications as are encompassed by the scope of the appended claims.

I claim:

1. A test field for an apparatus for testing the vision of a person as regards ability to work on video display terminals, in which indicia of different sizes and recognizability are presented to the person to be tested, characterized in that the indicia appear in a darker surrounding field, and in that brighter areas having a luminance of between 250–1000 cd/m$^2$ are provided adjacent the surrounding field, the luminance of the darker surrounding field being about one-fifth to one-eighth of the luminance of the indicia while the luminance of the indicia is about one-fifth to one-tenth of the luminance of the brighter areas.

2. A test field according to claim 1, characterized in that the test field is adapted to be one of projected or transilluminated.

3. A test field according to claim 2, characterized in that the indicia are in the form of at least one of numbers, letters, and symbols.

4. A test field according to claim 3, characterized in that the indicia are arranged within the test field in at least one horizontal row and are surrounded by strip-shaped darker surrounding areas which are adjoined above and below by brighter surface areas.

5. A test field according to claim 4, characterized in that the darker surrounding field has a luminance of about 10 cd/m$^2$, the indicia a luminance of about 70 cd/m$^2$ and the brighter areas a luminance of about 500 cd/m$^2$.

6. A test field according to claim 4, characterized in that the indicia are in the form of letters and numbers.

7. A test field according to claim 4, characterized in that the indicia are in the form of symbols, and in that the symbols are Landolt rings.

8. A test field according to claim 4, characterized in that the indicia are in the form of symbols, and in that the symbols are line-like gratings.

9. A test field according to claim 1, characterized in that a plurality of test fields are provided and arranged on a circular test disc with the indicia of diametrically opposed test fields being identical.

10. A test field according to claim 1, characterized in that the darker surrounding field has a luminance of about 10 cd/m$^2$, the indicia a luminance of about 70 cd/m$^2$ and the brighter areas a luminance of about 500 cd/m$^2$.

11. A test field according to claim 1, characterized in that the indicia are arranged within the test field in at least one horizontal row and are surrounded by strip-shaped darker surrounding areas which are adjoined above and below by brighter surface areas.

12. A test field according to claim 11, characterized in that the indicia are arranged within the test field in several rows and are surrounded in each row by strip-shaped darker surrounding areas which are each adjoined above and below by brighter surface areas.

* * * * *